United States Patent [19]

Steele

[11] Patent Number: 5,006,984
[45] Date of Patent: Apr. 9, 1991

[54] BONE/TISSUE ANALYZER AND METHOD

[75] Inventor: Charles R. Steele, Stanford, Calif.

[73] Assignee: Stanford University, Stanford, Calif.

[21] Appl. No.: 24,354

[22] Filed: Mar. 10, 1987

[51] Int. Cl.$^5$ .............................................. G06F 15/42
[52] U.S. Cl. ................................ 364/413.27; 128/744
[58] Field of Search .............. 364/415, 413.25, 413.27; 128/744, 740; 73/789

[56] References Cited

U.S. PATENT DOCUMENTS

| 4,297,884 | 11/1981 | Levequne et al. | 128/774 |
| 4,421,119 | 12/1983 | Pratt, Jr. | 128/774 |
| 4,511,984 | 4/1985 | Jumino et al. | 364/415 |
| 4,646,754 | 3/1987 | Seale | 128/774 |

OTHER PUBLICATIONS

Borders et al., (1977), Journal of Biomechanical Engineering, Transactions of the ASME 99:40–44.
Steele et al., in 1978 Advances in Bioengineering (Eberhart, Robert C., ed., ASME Publication, 1978), pp. 85–87.
Thompson et al., (1976) Med. Biol. Eng. 14:253–262.
Petersen, K. (1976), "In Vivo Determination of the Mechanical Properties of Bone", (Thesis, Dept. Applied Mechanics, Stanford University), pp. 1–82.
Steele, (1987) "Noninvasive Determination of Ulnar Stiffness from Mechanical Response—In Vivo Comparison of Stiffness and Bone Mineral", pp. 1–35.
Steele, "Instrument for Assessment of Bone Properties", presented at the Workshop on Advances, in NASA-Relevant Minimally Invasive Instrumentation, Apr. 25–27, 1984.
Petersen, (1977) "Noninvasive Determination of Bone Stiffness", (Dissertation, Dept. Applied Mechanics, Stanford University), pp.1–194.

Primary Examiner—Jerry Smith
Assistant Examiner—Kim Thanh Tbui
Attorney, Agent, or Firm—Peter J. Dehlinger

[57] ABSTRACT

Method and apparatus for measuring physical parameters, such as mass, and spring and damping constants, of a bone region of a human subject. The bone region is excited by a vibratory probe in a frequency range between about 70–1,600 Hertz, and the mechanical response of the tissue to the vibratory excitation is measured and converted to frequency-dependent force/displacement data. By correlating the force/displacement values determined from the force/displacement data with the behavior of a linear mechanical system having coupled bone and skin mass, the physical parameters which are contained in the equation of motion can be calculated.

11 Claims, 9 Drawing Sheets

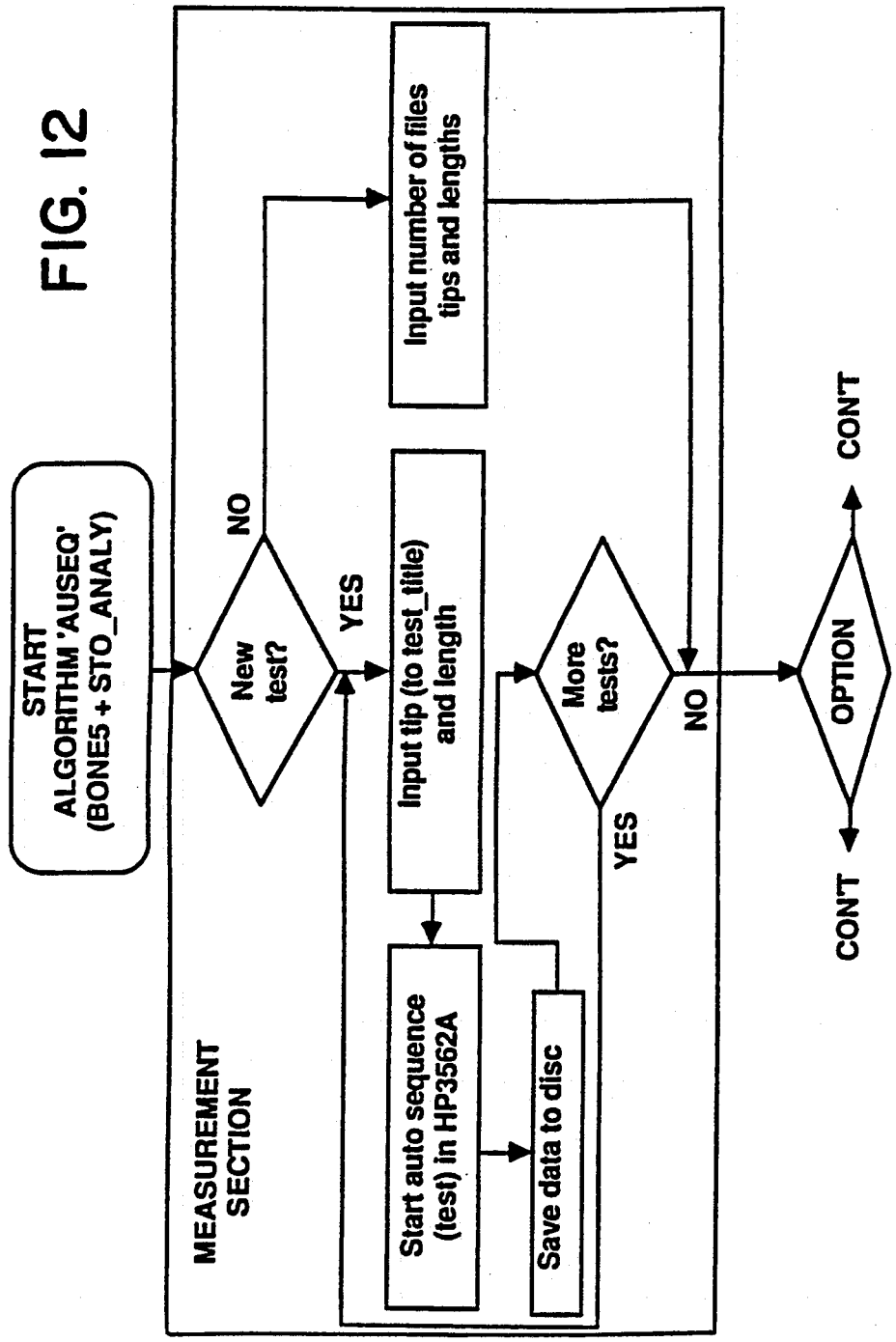

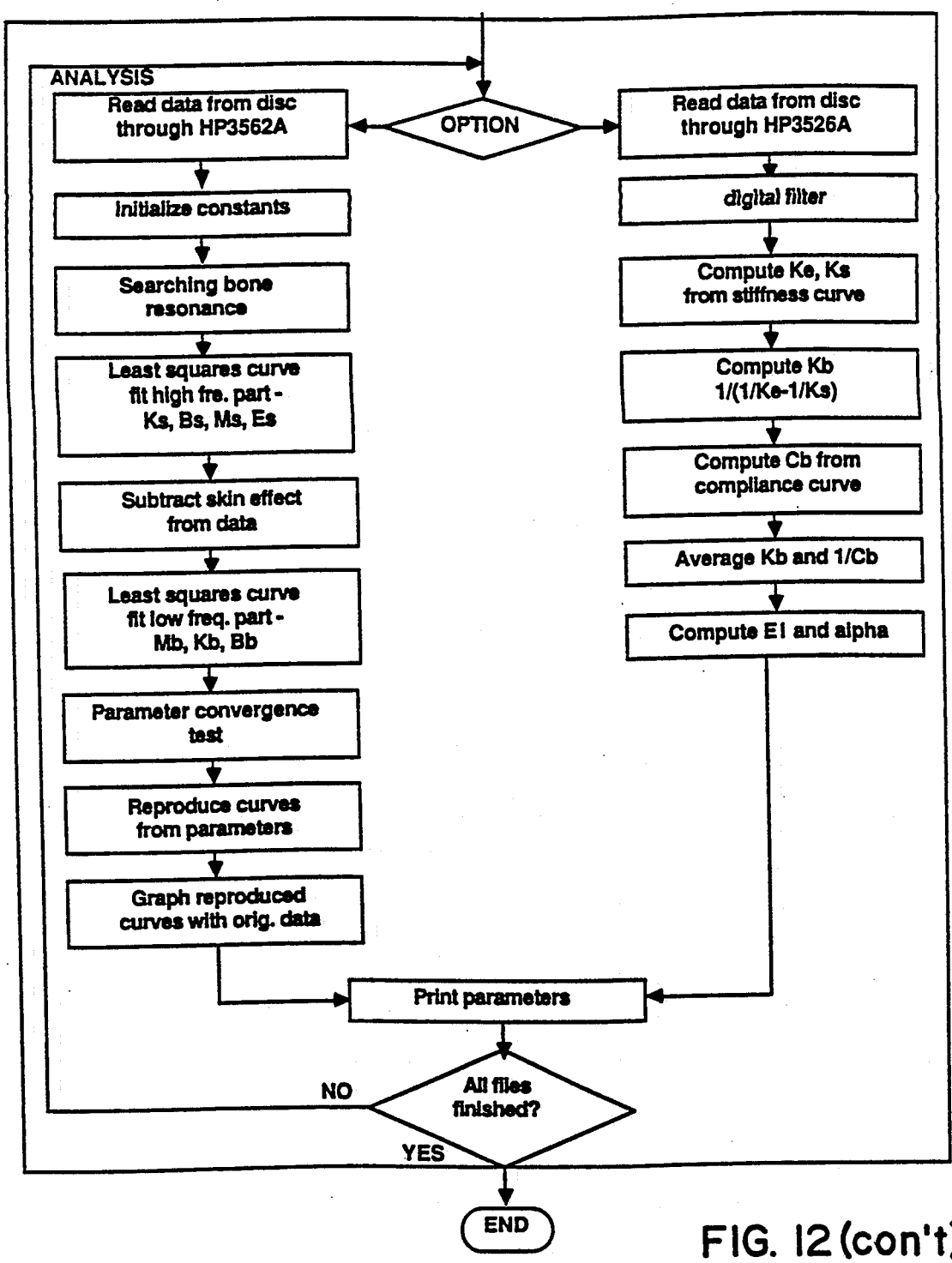
FIG. 12 (con't)

BONE/TISSUE ANALYZER AND METHOD

The project relating to this invention was funded in part by grant # NASA NAG-2-130 from the National Aeronautics and Space Administration. The government has certain rights in this invention.

1. FIELD OF THE INVENTION

The present invention relates to analyzing bone and soft-tissue characteristics, such as stiffness and based on the mechanical response of bone and overlying soft tissue to mechanical vibrations.

2. REFERENCES

Campbell, J. N., and Jurist, J. M. (1971) Mechanical impedance of the femur: a preliminary report, J. Biomechanics 4:319-322.

Orne, D., Borders, S., and Peterson, K. (1977). "Prediction of bending strength of long bones from measurements of bending stiffness and bone mineral content", J. Biomech., 99:40-44.

Peterson, K. (1975) Impedance device for in vivo determination of bone properties. Eng. Thesis, Stanford University.

Peterson, K. (1977) Noninvasive determination of bone stiffness. Ph.D. Dissertation, Stanford University.

Prentis, J. M., *Dynamics of Mechanical Systems*, Wiley and Sons. N.Y. (1980).

Steele, C. R., and Fleming-Gordon, A. (1978) Preliminary clinical results with 'SOBSA' noninvasive measurement of ulna bending stiffness. 1978 *Advances in Bioengineering*, ed. Eberhart, R. C., and Burstein, A. H. ASME Publication, 85-87.

Steele, C. R. (1984) Instrument for assessment of bone properties. Proc. Workshop on Advances in NASA-Relevant Minimally Invasive Instrumentation. Asilomar, Calif.

Steele, C. R. (1985) Noninvasive determination of bone properties from mechanical measurement. Proposal for Work 1985-86 Submitted to NASA-Ames. October 1985.

Stein, I. D., and Granik, G. (1982) The human tibia: static testing in bending by an in vivo method. Annals Biomed. Eng. 10:281-294.

Thompson, G. A., Orne, D., and Young, D. R. (1976) In vivo determination of mechanical properties of the human ulna by means of mechanical impedance tests: experimental results and improved mathematical model, Med. Biol. Eng. 14:253-262.

Wong, F. Y., Pal, S., and Saha, S. (1983) The assessment of in vivo bone condition in humans by impact response measurement. J. Biomechanics 16:849-856.

Young, D. R., Howard, W. H., Cann, C., and Steele, C. R. (1979) Noninvasive measures of bone bending rigidity in the monkey (M. nemestrina). Calcified Tissue Int'l 27:109-115.

Young, D. R., Niklowitz, W. J., and Steele, C. R. (1982). Tibial changes in experimental disuse osteoporosis in the monkey. Calcified Tissue Int'l 34:409-413.

3. BACKGROUND OF THE INVENTION

Information about the mechanical properties of bones is useful in many areas of orthopedic medicine. One area is in diagnosing and treating osteoporosis, a calcium-depletion disease prevalent in post-menopausal women. Another is in assessing the degree of healing which has occurred in a fractured bone. Loss of bone strength and stiffness by disuse is also a concern, where a patient has undergone long periods of immobilization. It is also desirable to monitor changes in bone mechanical properties during bone-related therapies, such as calcitonin treatment of osteoporosis, for purposes of evaluating and improving therapies.

One method for assessing the mechanical properties of bones which has been used clinically is photon absorptiometry, which provides a direct measure of bone mineral content (density). A single-beam method is used to monitor arm, heel, and lower bones of the leg, and a dual-beam technique, to monitor spine and femur. Although the method provides a good measure of bone mineral density, it does not reveal the condition of the bone matrix itself, i.e., the collagen-containing matrix which gives the bone its bending stiffness and load characteristics. For some conditions, like osteoporosis, bone mineral content appears to be a good indicator of bone health (Orne), and therefore photon absorption measurements are generally useful for diagnosing the disease state and monitoring therapy. However, for other conditions, such as fracture healing, bone mineral content may correlate only weakly with bone healing, and in these areas, the technique is of limited value.

Other limitations of single- and dual-beam photon absorptiometry include patient exposure to ionizing radiation, relatively long scan times (20 minutes or more) and complex and relatively expensive equipment.

Another bone-analysis approach which has been proposed heretofore is based on the response of bones to mechanical vibration. Attempts to use the mechanical measurement of bone resonance frequency for the evaluation of fracture healing and osteoporosis have been reported (Campbell). In theory, the method is capable of determining bone stiffness from the force and displacement measured during mechanical stimulation. This approach has been severely limited heretofore by soft tissue effects which tend to mask force and displacement values related to bone only. This problem may be partially solved by small vibrators which are pressed tightly against the tissue region of interest, in effect, establishing a more direct contact between the probe and the bone. However, mechanical stimulation with this arrangement tends to be painful, and in any case, does not totally eliminate soft tissue effects. An alternative, purely static approach which has been proposed (Stein) has severe problems of reproducibility. Another approach uses impact response (Wong). However, results are difficult to interpret and appear to be strongly dependent on soft tissue effects.

The inventor has previously proposed various mechanical response systems in which soft tissue effects can be reduced by (a) estimating soft tissue effects at higher frequency vibrations, where bone response is minimal, and (b) subtracting out soft-tissue effects from low-frequency measurements, as discussed in Petersen, 1975, 1977; Steele, 1978, 1984, 1985; and Young 1982, 1984. One such system, developed by the inventor and coworkers, has been tested on several hundred patients. Although the method has been applied with some success to many subjects, it has serious shortcomings where the subject is obese or shows heavy musculature. i.e.. where soft tissue effects are large. Also calculation times lend to be quite long, on the order of at least several minutes.

4. SUMMARY OF THE INVENTION

It is therefore a general object of the invention to provide, for analyzing bone mechanical properties, a method and apparatus which substantially overcome or reduce above-noted problems in bone-property analysis.

A more specific object of the invention is to provide such method and apparatus for determining bone stiffness and weight-loading properties in long skeletal bones.

Another object of the invention is to provide such method and apparatus which is relatively painless, rapid, and capable of accurate bone-stiffness measurements, even in human subjects with heavy soft tissue musculature or fat.

Still another object of the invention is to provide a system and method for analyzing soft-tissue mass and stiffness characteristics, as these apply to various tissue conditions of diagnostic interest.

The apparatus of the invention, for use in measuring bone stiffness and mass characteristics, includes a vibratory unit which is placed against the bone to be monitored and overlying soft tissue. The unit provides accurate response measurements for frequencies in the range between about 70–50,000 Hertz. For the global bone response the range between about 70 and 1,500 Hertz is of primary interest. The normal fundamental bone resonance occurs in the range 200–400 Hertz. The high frequency range between about 1,000–1,600 Hertz is necessary to identify soft tissue properties, while the low frequency range between about 70–200 Hertz provides information on bone and skin in series. The intermediate range between about 200–800 Hertz is necessary to identify bone mass.

The vibratory unit contains transducers which output tissue-response signals related to force and acceleration in the frequency range between about 70–1,600 Hertz. These signals are digitized and broken down into frequency-dependent components, including frequency dependent force and displacement components, by a spectral analyzer in the apparatus, to yield force/displacement data, typically including real and imaginary force displacement curves. The physical parameters of interest are determined by correlating force/displacement values determined from the force/displacement data with the behavior of a linear mechanical system having coupled bone and skin masses, and whose equation of motion contains the physical parameters to be determined.

In a preferred embodiment, the vibratory unit includes an electromagnetic exciter or shaker, a probe attached to the exciter for vibratory movement therewith, and force and acceleration transducers carried on the probe. The probe has a concave contact surface for improved contact between the vibrating unit and the tissue region against which the contact surface is placed.

The calculation of physical parameters is carried out by a computer which may follow one of three different algorithms for determining bone spring constant ($K_b$). The first algorithm, referred to herein as "STO-ANALY", is followed when soft-tissue damping effects are small. The algorithm uses high-frequency (above about 1,000 Hertz) and low-frequency (below about 400 Hertz) force/displacement data to estimate $K_s$ and $K_e$ values, respectively, where $K_s$ is the soft-tissue spring constant $K_e$ is the spring constant for combined bone and soft tissue. The $K_b$ value is calculated from the estimated $K_e$ and $K_s$ values, and loW-frequency force/displacement data.

The second algorithm, referred to herein as "BONE 5", is followed when relatively large soft-tissue damping effects are anticipated, or observed from the high frequency slope of the real force/displacement curve. The algorithm operates first to estimate $K_s$, the soft-tissue spring constant, $M_s$, the effective soft-tissue mass, and $B_s$, the damping coefficient(s) associated with the soft tissue, by least-square curve fitting to the high-frequency region of the real and imaginary force/displacement curves. These values yield an equation of motion for soft tissue which, when subtracted from the low-frequency regions of the force/displacement curves, yields corrected low-frequency curves. Curve fitting to the corrected low-frequency curves gives first-approximation values for $K_b$, $M_b$, the mass of the bone, and $\beta_b$, the bone-damping factor. The equation of bone motion obtained from the first-approximation bone parameters is then subtracted from the high-frequency regions of the force/displacement curves, yielding corrected high-frequency curves which are now used to estimate second-approximation $K_s$, $M_s$ and soft-tissue damping coefficients by curve fitting. The successive approximations are continued until changes in the estimated $K_b$ value converge to a desired limit.

The third algorithm, referred to as "POLE-ZERO", is similar to the BONE 5 algorithm, except that the curve fitting capability of the analyzer is utilized to calculate the poles and zeros of the force/displacement transfer function. The bone and skin physical parameters are then calculated from the determined transfer function pole and zero values.

The second and third algorithms calculate soft-tissue mass and stiffness characteristics which can be used for analysis of soft-tissue conditions or diseases, independent of bone parameter measurements.

The invention also includes a method for determining bone stiffness, using the machine-assisted steps just described, and more generally for measuring bone stiffness and mass and soft-tissue stiffness and mass characteristics.

These and other objects and features of the invention will become more fully apparent when the following detailed description of the invention is read in conjunction with the accompanying drawings.

5. BRIEF DESCRIPTION OF THE DRAWINGS

FIG. 12 is a flow chart of the combined algorithms for STO-ANALY, based on the behavior of the FIG. 10 mechanical system, and BONE 5, based on the behavior of the of the FIG. 11 mechanical system;

DETAILED DESCRIPTION OF THE INVENTION

I. Bone/Tissue Analyzer Apparatus

Figure 1:
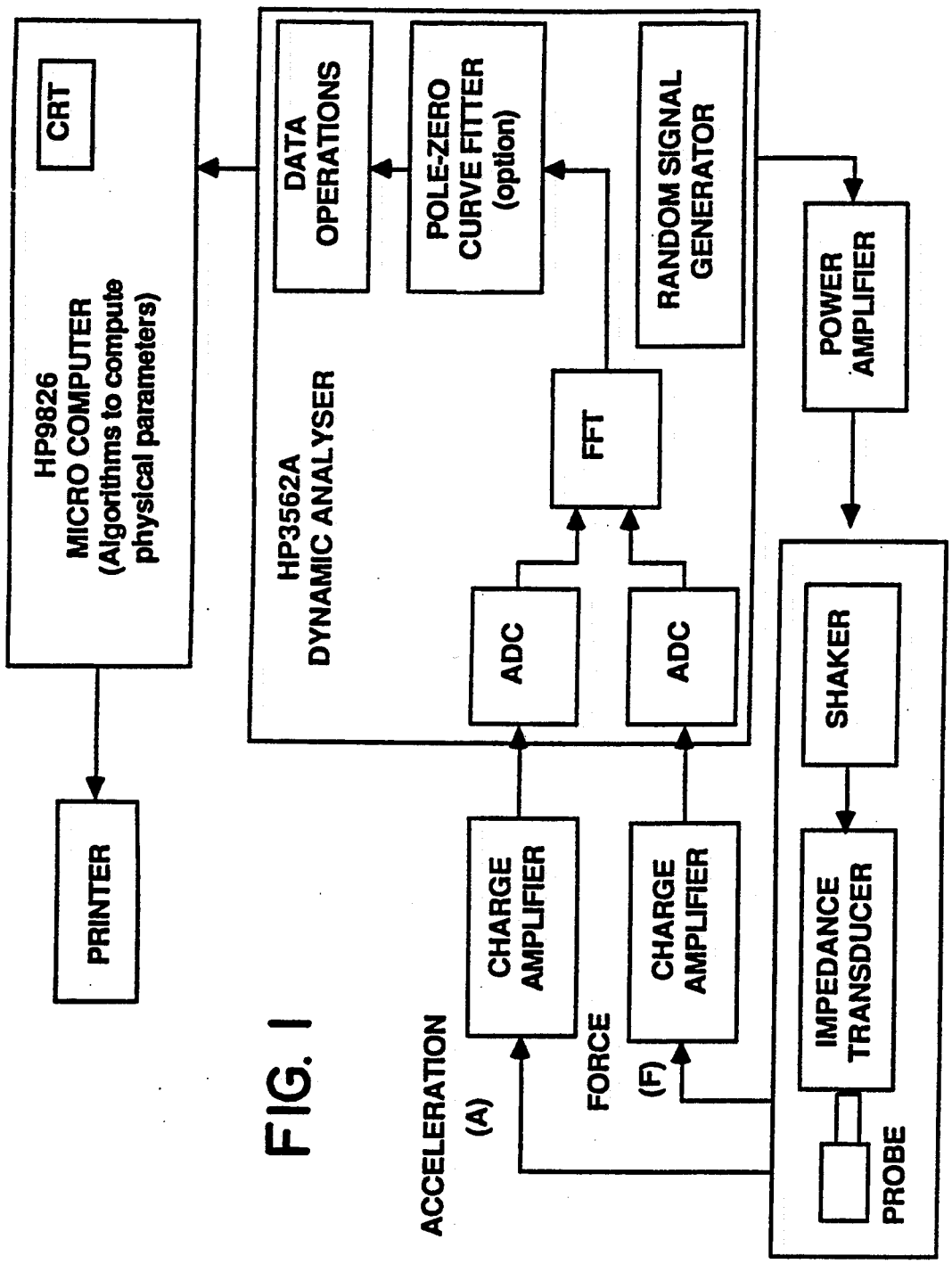
FIG. 1 is a block diagram of a bone/tissue analyzer apparatus constructed according to the invention.

FIG. 1 shows the bone/tissue analyzer apparatus of the invention in block diagram form. The apparatus, indicated at 14, includes a vibration unit 16 having a vibration exciter or shaker 18, a probe 20 which functions to vibrate the tissue region of interest, and an impedance head 22 which is interposed between the shaker and probe. In operation, the shaker is driven by a frequency generator 24 whose output is a white-noise signal containing frequency components in the range between about 30–1,600 Hertz. The generator signal is supplied to the vibrator through a power amplifier 26. The impedance head has force (F) and acceleration (A) transducers indicated at 27 and 29, respectively, which output analog signals relating to the force and acceleration response of the tissue to mechanical vibration. Details of the vibration unit will be discussed further below with respect to FIGS. 2 and 3.

Signals from two impedance-head transducers 27, 29, related to force and acceleration are supplied through signal amplifiers 28, 30, respectively, in a spectral analyzer which is shown in solid lines 32. The analyzer has two analog-to-digital converters (ADCs) 34, 36, for digitizing the force and acceleration analogue signals, respectively, from the vibratory unit, and a microprocessor for carrying out data analysis operations. More specifically, the analyzer transforms the two input signals with a fast Fourier transform (FFT), to obtain a spectral decomposition of both force and acceleration signals, and performs a double integration of the acceleration components, to determine corresponding tissue displacement components over the low and high excitation frequencies.

The output of the analyzer—which includes data relating to the frequency decomposition of the force and displacement (or acceleration, from which displacement is calculated)—is referred to herein as force/displacement data. Typically, the data is output in the form of real and imaginary force/displacement curves which plot the real and imaginary portions of the frequency-dependent tissue response as a function of excitation frequency over the frequency range of about 70–1,600 Hertz. Typical real and imaginary force displacement curves are shown (jaqged curves) in FIGS. 13A and 13B, respectively. Microprocessor systems in the analyzer which carry out FFT and force/displacement calculation operations are indicated at 38, 40, respectively in FIG. 1. One preferred analyzer, which also includes signal generator 24, is an HP3562A Structure Dynamic Analyzer, available from Hewlett-Packard Instruments (Palo Alto. Calif.). This analyzer also includes a pole-zero curve fitter 39 which determines pole-zero polynomial values by curve fitting to the real and imaginary force/displacement curves, as will be considered in Section IIID below.

With continued reference to FIG. 1, the apparatus further includes a computer or computational means 42 for calculating bone stiffness, mass, and load carrying values, from the force/displacement data supplied by analyzer 32. The computer may be a conventional microcomputer programmed to carry out the bone-value calculations by the algorithms discussed below in Section III below, or preferably a dedicated microprocessor designed to execute one or more of the algorithms. The design and operation of the computer will become clear from the algorithms discussed below.

Completing the description of FIG. 1, the computer is connected to a suitable recording device, such as printer 44, for recording and displaying information relevant to bone analysis. Typically the display shows the force/displacement curves, plotted as a function of excitation frequency (from analyzer 32), bone stiffness and weight loading values calculated by the computer, and relevant patient data.

Figure 2:
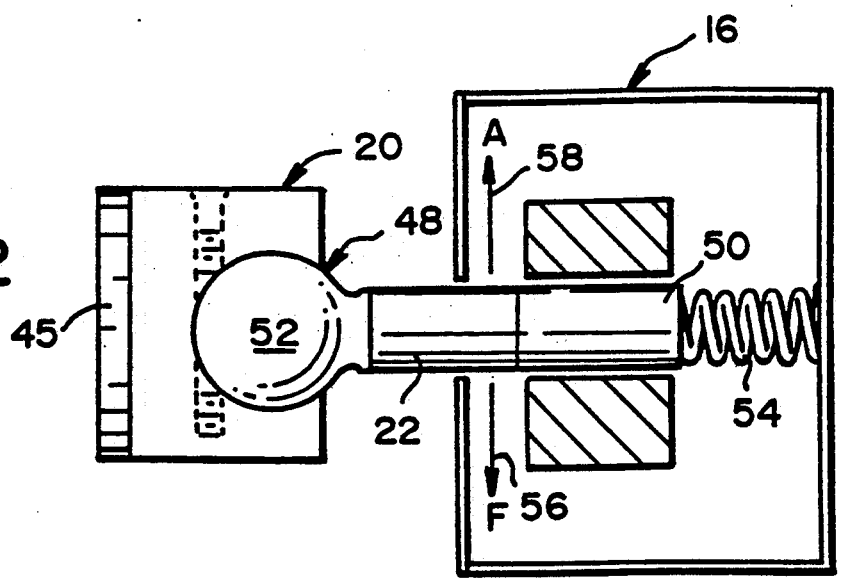
FIG. 2 is a side sectional view of a vibrator unit constructed according to the invention.
Figure 3:
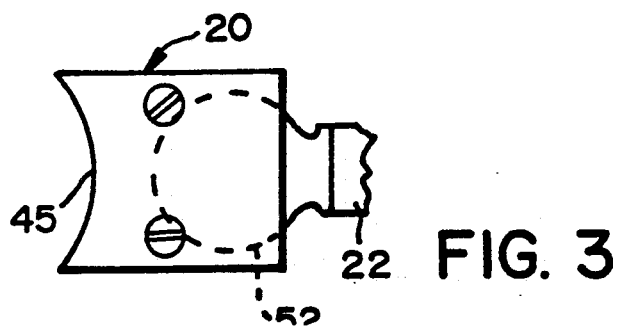
FIG. 3 is a top view of the probe in the FIG. 2 unit, taken along line 3—3 in FIG. 2, and shown contacting a mid region of a forearm.

FIGS. 2 and 3 show portions of vibrator unit 16 such as shown in FIG. 1 having a self-adjusting probe 20. As seen in FIG. 3, the probe has a concave tissue-contact surface 45 against which the convex surface of an arm or bone tissue region, such as region 46, is nested during tissue excitation. The total contact area of the probe is typically between about 0.5–2 cm². The probe is carried by means of a ball-in-socket coupling 48 at the end of impedance head 22 which in turn is rigidly attached to a vibratory piston 50 in the shaker. As seen in FIG. 2A, the probe is composed of top and bottom symmetrical halves which are bolted together, forming a socket for a ball 52 carried at the distal end of the impedance head.

With continued reference to FIG. 2, the end of the shaker opposite the probe is attached to a "constant-force" spring 54 which maintains a static preload force of about 10 Newtons, independent of the displacement of the shaker. A second option is for the operator to hold the shaker by hand in a vertical position, in which case the weight of the shaker supplies the static preload, without need for the axial spring. In either case, there is a static force of the probe against the tissue region being excited, which has a magnitude of about 10 Newtons.

The impedance head is a conventional transducer device having both force and acceleration transducers, indicated in the figure by transducer outputs 56 and 58, respectively. The shaker and impedance heads used in forming the vibrator unit are preferably commercial devices, such as a Bruel and Kjaer vibration exciter 4810, and impedance head 8001 supplied by the same company.

II. Mechanical Response Measurements

Figure 4:
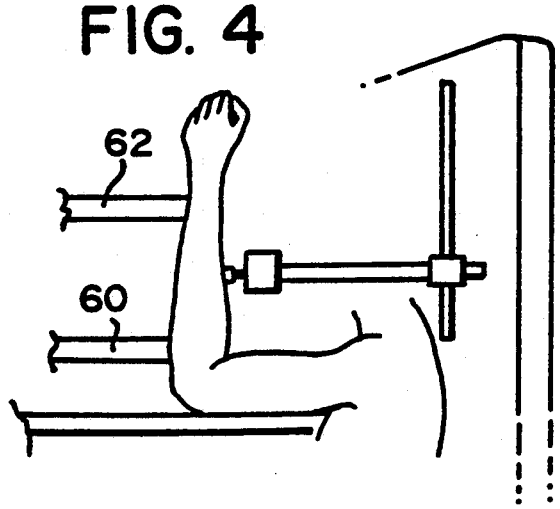
FIGS. 4 and 5 show preferred test configurations for determining bone stiffness in the arm (radius) and lower leg (tibia), respectively.
Figure 5:
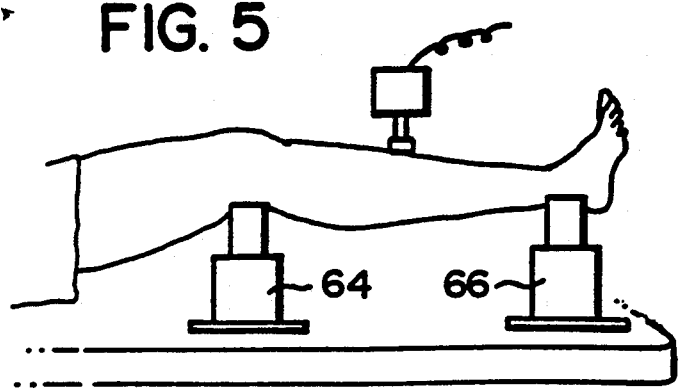

FIGS. 4 and 5 show preferred configurations for making arm and leg bone stiffness measurements, according to the invention. In each case, the bone region of interest is placed in a position at which it is supported at its upper and lower ends by a pair of fixed supports. In the configuration shown in FIG. 4, where bone stiffness in the radius is being measured, the subject's elbow is supported on a table, and the elbow wrist are placed against supports 60, 62. The position of the vibratory unit is adjusted vertically to about the midpoint of the forearm, and laterally to bring the probe into contact with and under slight pressure against the soft tissue which immediately overlies the radius, with the supports resisting the slight biasing of the probe.

In the configuration shown in FIG. 5, where bone stiffness in the tibia is being measured, the back of the subject's lower leg is placed between knee and ankle supports 64, 66, respectively, as shown, and the probe position is adjusted laterally to contact the mid portion of the shin, and vertically, to exert slight pressure on the contacted tissue region. Either the vertical (FIG. 4) or horizontal (FIG. 5) position of the bone under test may be used for the bones of the arms or the legs.

During the excitation period, which is typically about 5 seconds, the mechanical response of the tissue, as detected by the impedance head, is converted to force and acceleration signals by the impedance head transducers, and these signals are processed by analyzer, as above, to produce the desired force/displacement data which is used for making bone stiffness calculations. The excitation period may be extended to obtain two or more force/displacement data curves, for averaging purposes. However one measurement is usually adequate.

Figure 6:
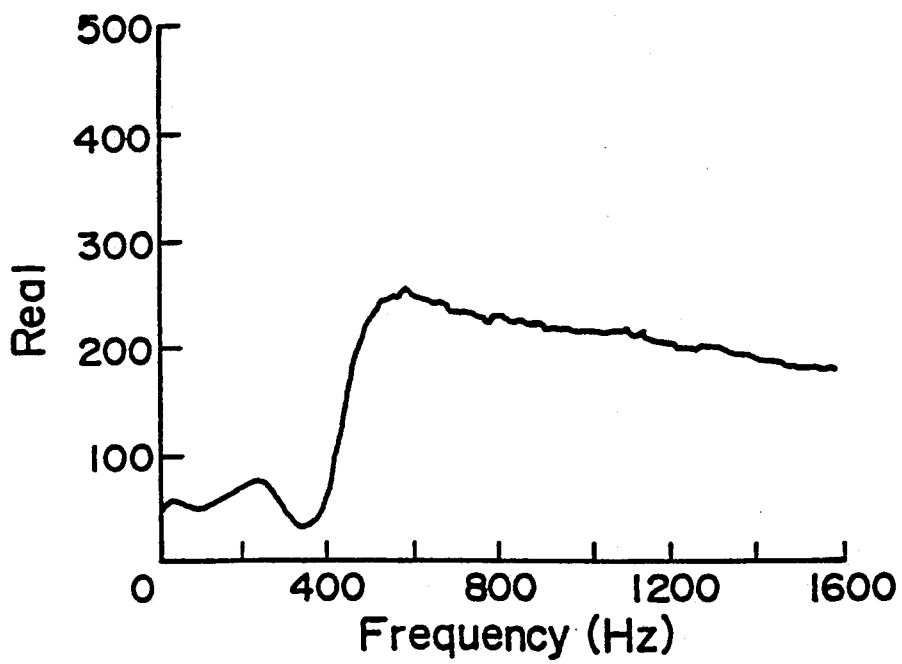
FIGS. 6 and 7 are exemplary real force/displacement curves, showing the force/displacement ratio as a function of vibration frequency, in tissue regions having small soft-tissue mass and damping effects, (FIG. 6) and relatively large soft-tissue mass and damping effects (FIG. 7)

FIG. 6 shows the real portion of a typical force/displacement/displacement curve obtained from a forearm (ulna) measurement performed as above. The lower-frequency region of the curve—below about 400 Hertz—represents force and displacement response from both the bone and overlying soft tissue. The sharp rise in the curve, between about 400–600 Hertz reflects the main system resonance, and the increasing contribution of soft-tissue alone, which has characteristic high force/displacement values. The curve shows a slow decrease in displacement/force between about 600–1,600 Hertz, to a constant value. This behavior in the high-frequency region of the curve indicates that soft-tissue mass and damping effects are not significant. Accordingly, bone stiffness and loading values can be calculated by approximation to a relatively simple mechanical system which does not include damping between soft-tissue and bone masses, as will be described in Section IIIB. This type of force/displacement response is usual in test subjects who do not have high fat or muscle bulk.

Figure 7:
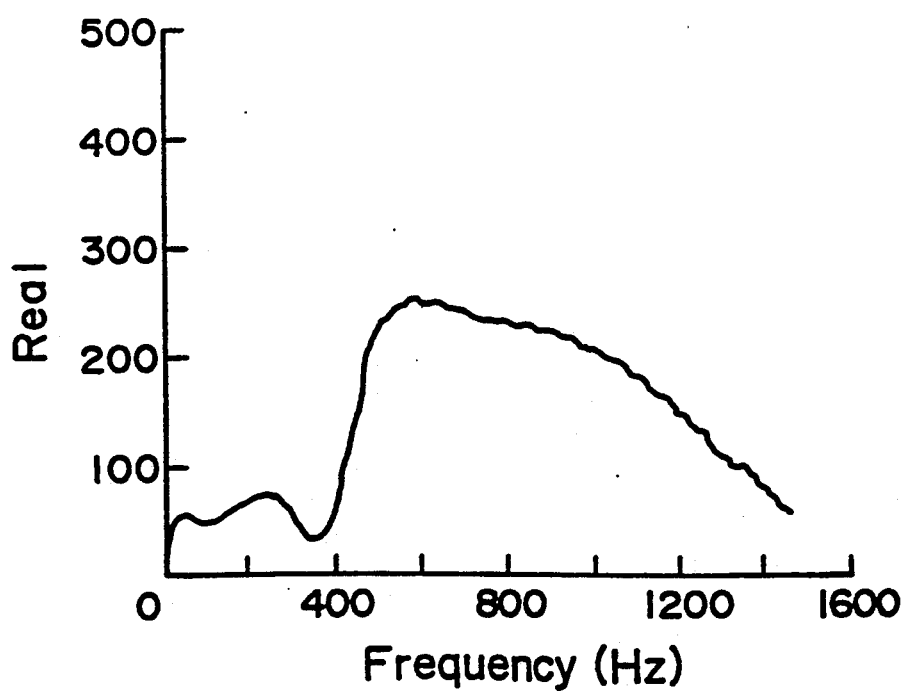

FIG. 7 shows the real portion of a more complex force/displacement curve obtained from an obese test subject. Here the high-frequency region of the curve shows a substantially non-linear drop in displacement/force over the 800–1,600 Hertz range, indicating significant tissue-damping and mass effects. Accordingly, the bone stiffness and bone loading values are calculated by approximation to a more complex mechanical system in which soft-tissue damping effects are considered. As will be seen in Section IIIC and D, the more complex algorithms used in the tissue-damping case also generate, as a biproduct of the analysis, mass and damping values related to both bone and soft tissue.

III. Mechanical Response Calculations

A. Stiffness and Weight-loading Parameters

Figure 8:
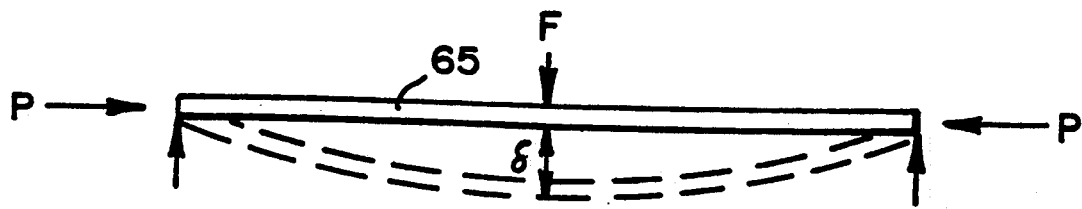
FIG. 8 illustrates force and displacement relations in a beam, such as a long bone.

One fundamental bone property which can be measured in the method of the invention is lateral stiffness. The property derives from the behavior of an idealized beam under lateral force, as illustrated in FIG. 8. With reference to the figure, a lateral force F applied to the middle of a long beam 65 produces a deflection $\delta$. The ratio of force to deflection, i.e., $F/\delta$, is the stiffness k, which can be computed from the formula that is well-known for a straight beam with constant properties:

$$\frac{F}{\delta} = K = \frac{48EI}{L^3} \qquad (1)$$

Here EI is the fundamental stiffness of a section of the beam, consisting of Young's modulus E, which is an intrinsic material property, and the cross-sectional moment of inertia I, which indicates the amount of material and how it is distributed; and L is the length of the beam. Thus by determining k, and knowing L, the fundamental stiffness property EI of the bone can be calculated.

In addition to lateral stiffness, which gives information about the bone strength and material distribution, it is also useful to consider the load-carrying capacity of the bone being measured. In every structural framework there must be tensile and compressive members, and in vertebrates, the long bones have the fundamental physiological function of serving as the compressive members. For the simplified case of the uniform beam shown in FIG. 1, the formula for the limiting buckling force is:

$$P_{cr} = EI\left(\frac{\pi}{L}\right)^2 \text{ or,}$$

from equation 1:

$$P_{cr} = \frac{KL\pi^2}{48} \qquad (2)$$

In the normal environment, the loads on the skeleton are generally proportional to body weight. This suggests that the ratio of body weight to limiting buckling force, i.e., W/P, is a useful characterization of bone strength. This weight-bearing parameter $\alpha$ is defined as $$\alpha = \frac{W}{P_{cr}}$$

or, from equation 2:

$$\alpha = \frac{48 \, W}{\pi^2 KL} \qquad (3)$$

In summary, by measuring the force F applied to the bone, and bone deflection, it is possible to determine bone stiffness k, and from this EI and $\alpha$ parameters, using known bone length and body weight values.

B. First Algorithm: STO-ANALY

The problem of making meaningful force and displacement measurements on bones is, of course, more difficult than direct measurements on a beam, due to the masking effect of soft tissue. The problem has been approached in the present invention by modeling a complex bone/soft tissue system, and analyzing the force/displacement behavior of the system, as a function of excitation frequency. From this analysis, algorithms which provide efficient bone and soft-tissue stiffness calculations, in situations of either low or high soft-tissue bulk, have been developed.

Figure 9:
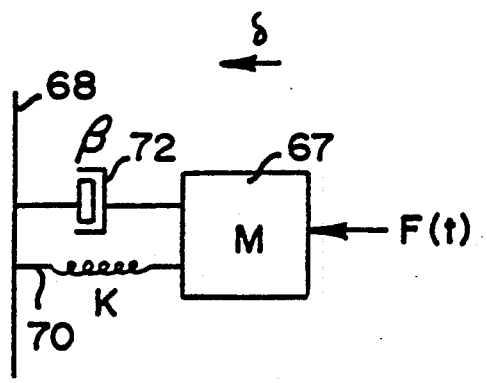
FIG. 9 shows a simple one-mass mechanical system which approximates the motion of soft-tissue mass in the systems shown in FIGS. 10, 11, and 14.

The models which will be considered are second-order linear systems of the type illustrated most simply in FIG. 9. The system illustrated here contains a mass (M) 67 which is coupled to a fixed reference structure 68 by means of a spring 70 having a spring constant K, and a viscous damper 72 having a damping coefficient $\beta$. Here it is noted that the spring constant K is equivalent to the stiffness value k in equation 1, i.e., K is a proportionality constant which relates the deflection of the mass to applied force. The equation of motion of the system, when a force F is applied to the mass, producing a deflection $\lambda$, is given by:

$$M\ddot{\delta} + \beta\dot{\delta} + K\delta = F(t) \quad (4)$$

where $\dot{\delta}$ and $\ddot{\delta}$ are the first and second time derivatives of $\delta$, respectively. The reader is referred to a standard text in the field (e.g., Prentis, pp 220–228) for a discussion of second order linear systems and their solutions. Assuming a harmonic excitation with a frequency $\omega$, equation 4 has the general solution given in equation 5, which allows the equation of motion to be expressed in terms of F/$\lambda$, as in equation 6. As seen, the solution has both real (K-MW$^2$) and imaginary (W$\beta$) terms:

$$(M(-W^2) + j\beta W + K)\delta = F(t) \quad (5)$$

$$K - MW^2 + j\beta W = F(W)/\delta \quad (6)$$

Figure 10:
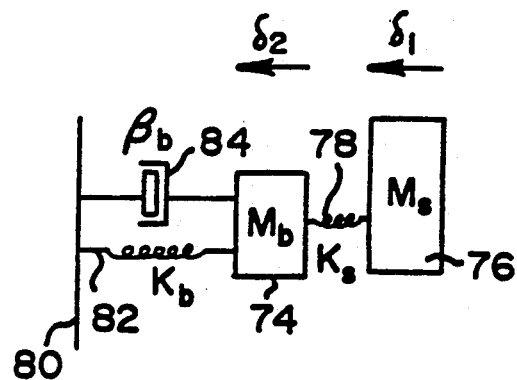
FIG. 10 illustrates a second-order, linear mechanical system used in analyzing tissue response characteristics of bone and the overlying soft tissue region, in a simplified case where soft-tissue damping effects can be ignored.

Equation 6 describes the motion of a simple one-mass system (FIG. 9) in response to a harmonic force. FIG. 10 shows a simple two-mass system whose motion is intended to approximate the behavior of coupled bone and soft-tissue masses, where soft-tissue damping effects are ignored. The system includes a bone mass 74 ($M_b$) which is coupled to a soft-tissue mass 76 ($M_s$) by a spring 78 having a spring constant $K_s$, representing the "stiffness" of the soft tissue. The bone mass is attached to a fixed reference structure 80 by a spring 82 with constant $K_b$ (representing bone stiffness), and a viscous damper 84 with coefficient $\beta_6$ (representing bone damping). If $\delta_1$ and $\delta_2$ are displacements of $M_s$ and $M_b$, respectively, then $$K_s(\delta_1 - \delta_2) = F(t) \quad (7)$$

where F is the force applied to $M_s$ as shown. From equation 6, which relates the displacement $\delta_2$ of the bone mass to an applied force, and assuming that the system is excited by a harmonic force of $F(\omega)$, it follows that:

$$\delta_1 - F/(K_b - M_b\omega^2 + j\beta\omega) = \frac{F(\omega)}{K_s} \quad (8)$$

or:

$$\frac{F(\omega)}{\delta_1} = K_e = 1/\left(\frac{1}{K_s} + \frac{1}{K_b - M_b\omega^2 + j\beta\omega}\right) \quad (9)$$

where $K_e$ is the spring constant of the coupled system.

Values of $K_s$ and $K_b$ are determined from the force/displacement curves generated as above. As has been indicated above, the force/displacement curves above about 800 Hertz reflect predominantly soft-tissue response, allowing $K_s$ to be calculated from Equation 9, ignoring the terms relating to bone parameters. Specifically, at frequencies above about 1,00 Hertz, $K_s = F/\delta$, and a measured value of F/$\delta$ from the high-frequency region of the real force/displacement curve (exemplified in FIG. 6) can be used to determine $K_s$. The STO-ANALY algorithm operates to determine a number of real force/displacement values between about 800 and 1,600 Hertz, and these values are averaged to give a final $K_s$. In addition, the inverse displacement/force curve is similarly analyzed to determine a compliance soft-tissue constant $C_s$.

From equation 9, it is seen that $K_e$ can be estimated from the force displacement curve in a low-frequency region of the curve where both bone and soft-tissue effects contribute to the overall stiffness of the tissue region being measured. In the STO-ANALY algorithm, $K_e$ is determined from the maximum force/deflection value in the low-frequency portion of the real part of the force/displacement curve, indicated at m in the FIG. 6. At this frequency, where $\omega$ is relatively low, frequency-dependent mass ($M_s$) and damping effects are small, yielding the simplified equation:

$$\frac{F}{\delta_1} = 1/\left(\frac{1}{K_s} + \frac{1}{K_b}\right) = K_e \quad (10)$$

This equation is readily solved for $K_b$ from the previously estimated $K_s$ and $K_e$ values. As above, a compliance $C_e$ value is also determined from the displacement/force curve. Once $K_b$ is known, bone stiffness EI and the weight bearing parameter are readily calculated from equations 1–3.

FIG. 12 shows a flow diagram of the STO-ANALY algorithm used in (a) measuring tissue mechanical response, and (b) using force/displacement curves determined from the response to determine bone stiffness, EI, and the weight-loading coefficient, $\alpha$. The upper portion of the figure included in box 100 shows the measurement section which is applicable to both the STO-ANALY and BONE 5 algorithms, and the lower section, the steps in both the STO-ANALY algorithm (at the right in the figure and indicated at 104) and the BONE 5 algorithm (at the left in the figure and indicated at 106).

Initially, the program is supplied data relating to bone length and body weight. Force/displacement data is generated from the mechanical response of the tissue to broad-spectrum excitation, as described in Section II. The real force/displacement curve is then analyzed, either visually by the operator, or automatically by a curve-analysis subroutine in the microprocessor, to determine the frequency-dependent behavior of the curve in the high frequency range. Assuming the curve shows a relatively slow, linear decrease in force/displacement ratio in this region, the STO-ANALY algorithm is suitable, and the program may be switched to this algorithm, at the "Option" step in the flow diagram indicated at 102. The STO-ANALY program operates, as outlined above, to estimate $K_s$ and $K_e$ values from high- and low-frequency regions of the real force/displacement curve, as outlined above. From these values, $K_b$ and $C_b$ (bone compliance) values are determined, and the calculated $K_b$ and $C_b$ values are averaged to determine a final $K_b$. Finally, EI and $\alpha$, the weight-loading parameter, are determined from equations 2 and 3. Typical run time required for data analysis and computation of bone stiffness parameters is about 1 minute. FIG. 6 shows a typical force displacement curve from a tissue region having small soft-tissue mass and damping effects. The algorithm just described is embodied in the computer program attached hereto as Appendix A, which combines the STO-ANALY and BONE 5 programs. The program is written in BASIC language, and is intended to be run on a Hewlett-Packard HP9826 computer.

C. Second Algorithm: BONE 5

This section describes a more complex linear system and solution algorithm which is suitable for computing bone stiffness and other bone and soft-tissue parameters when significant soft tissue mass and damping effects are present. As noted above, soft tissue damping effects are observed in test subjects with high fat or muscle bulk, and are characterized by a substantially non-linear fall in the real force displacement curve in the high-frequency region of the curve, as typified by the curve in FIG. 7.

The bone/tissue analyzer apparatus may be designed, i.e., programmed, to switch automatically between the STO-ANALY and BONE 5 algorithms after analyzing the high-frequency region of the real force/displacement curve. Alternatively, the apparatus may be designed for operator selection of one of the two algorithms, based on the operator's evaluation of the soft-tissue mass of the test subject and/or the shape of the high-frequency portion of the real force/displacement curve.

Figure 11:
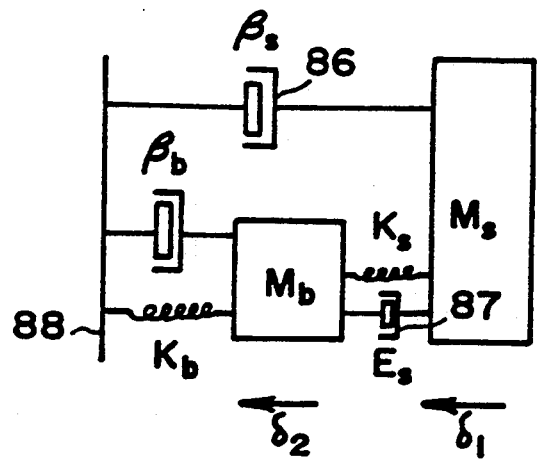
FIG. 11 illustrates a second-order, linear mechanical system used in analyzing tissue response characteristics of bone and the overlying soft tissue region, in a more complex case where soft-tissue damping effects are considered.

The second-order linear system which is used in modeling the behavior a bone and soft tissue masses with soft-tissue damping is shown in FIG. 11. The system includes, in addition to the elements shown in FIG. 10, a damper 86 coupling the soft-tissue mass $M_s$ to a reference structure 88, and a damper 87 coupling the bone and skin masses. Damper 86, which is characterized by a damping factor $\beta_s$, represents frequency-dependent viscous damping which functions to damp out oscillations in the system. Damper 87, which is characterized by a material damping factor $E_s$, represents frequency-independent material viscosity which modulates the soft-tissue spring coupling constant $K_s$.

The solution of the equation of motion of the system is approached by an iterative curve-fitting method which is outlined in the BONE 5 algorithm at the left in the Analysis section of the FIG. 12 flow diagram. The initial steps in the bone measurement test, including initial data input and inputting of force/displacement data, follow those used in the STO-ANALY algorithm. The high-frequency region of the real force displacement curve is analyzed for appreciable soft-tissue mass and damping effects, as evidenced by the a relatively large and non-linear decline in force/displacement ration within this region. If this behavior is observed, either by the operator or by automated curve analysis, the program is switched to the BONE 5 algorithm, for successive estimations of skin and bone parameters, according to the method outlined above.

With reference to the BONE 5 algorithm shown in the figure, the parameters relating to soft-tissue motion only ($M_s$, $K_s$, $\beta_s$, and $E_s$) are determined initially by least-square curve fitting to the high-frequency regions of the real and imaginary force/displacement curves, preferably in the region between about 800–1,600 Hertz, where bone motion effects are ignored as a first approximation. The equation of motion of the soft-tissue portion of the system is:

$$-M_s\omega^2 + j\beta_s\omega + K_s(1 + jE_s) = \frac{F(\omega)}{\delta_1} \tag{11}$$

or, combining the real and imaginary terms:

$$-M_s\omega^2 + K_s + j(\omega\beta_s + E_s) = \frac{F(\omega)}{\delta_1} \tag{12}$$

In the curve fitting algorithm, the $M_s$ and $K_s$ terms are determined by least-square fitting to the real force/displacement curve, and the $\beta_s$ and $E_s$ terms by curve fitting the imaginary force/displacement curve. Least-square curve fitting methods, such as those incorporated into the BONE 5 program given in Appendix A, are well-known and are not detailed here.

The contribution of soft tissue motion is now subtracted from the lower-frequency portions of the real and imaginary curves, according to equation 13 below, where $\delta_1$ and $\delta_2$ are the displacements of the t-tissue and bone masses, respectively, and $\delta_1/F$ is determined from equation 12, using the estimated soft-tissue parameter values. The subtraction gives the equation of bone mass only, according to equation 14:

$$\frac{\delta_1}{F} + \frac{\delta_2}{F} = \frac{\delta}{F} \tag{13}$$

$$\frac{\delta_2}{F} = \frac{\delta}{F} - \frac{\delta_1}{F} = 1/(M_b\omega^2 + j\beta_b\omega + K_b) \tag{14}$$

Least-square curve fitting of the real and imaginary parts of equation 14 to the subtracted, real and imaginary force/displacement curves in the region between about 70–800 Hertz is now performed to estimate values for $M_b$, $K_b$ and $\beta_b$. These values, in turn, are used to refine the skin-response parameters, by subtracting bone-motion effects from the higher-frequency portions of the real and imaginary force/displacement curves, and re-estimating $M_s$, $K_s$, $\beta_s$, and $E_s$ by least-square curve fitting to the corrected high-frequency portions of the curves. The curve subtraction is made substantially as above, by subtracting the "solved" equation of motion from bone from the force/displacement curve, as indicated in equation 15.

$$\frac{\delta_1}{F} = \frac{\delta}{F} - \frac{\delta_2}{F} = 1/(-M_s\omega^2 + K_s + j(\omega\beta_s + E_s)) \tag{15}$$

The refined soft-tissue parameter values are used to estimate new bone parameters, as above, using equations 13 and 14. At each iteration, the newly estimated $K_b$ is compared with last-estimated $K_b$, to determine convergence of $K_b$ values to a selected level, typically less than 1% convergence between the two values. If the desired convergence is achieved, the program prints the bone and skin data, and plots of the measured and calculated force/displacement curves. The measured and calculated force/displacement curves are compared for fit, and if necessary, the bone parameters are modified to achieve a better fit, according to the scheme shown at 106 in FIG. 12. From the final estimated skin stiffness values, EI and α values are calculated from equations 2 and 3. The total program, which is embodied in the program attached hereto as Appendix B, requires about five minutes of running time. The program is written in BASIC language and runs on a Hewlett-Packard Model HP9826 computer.

Figure 13:
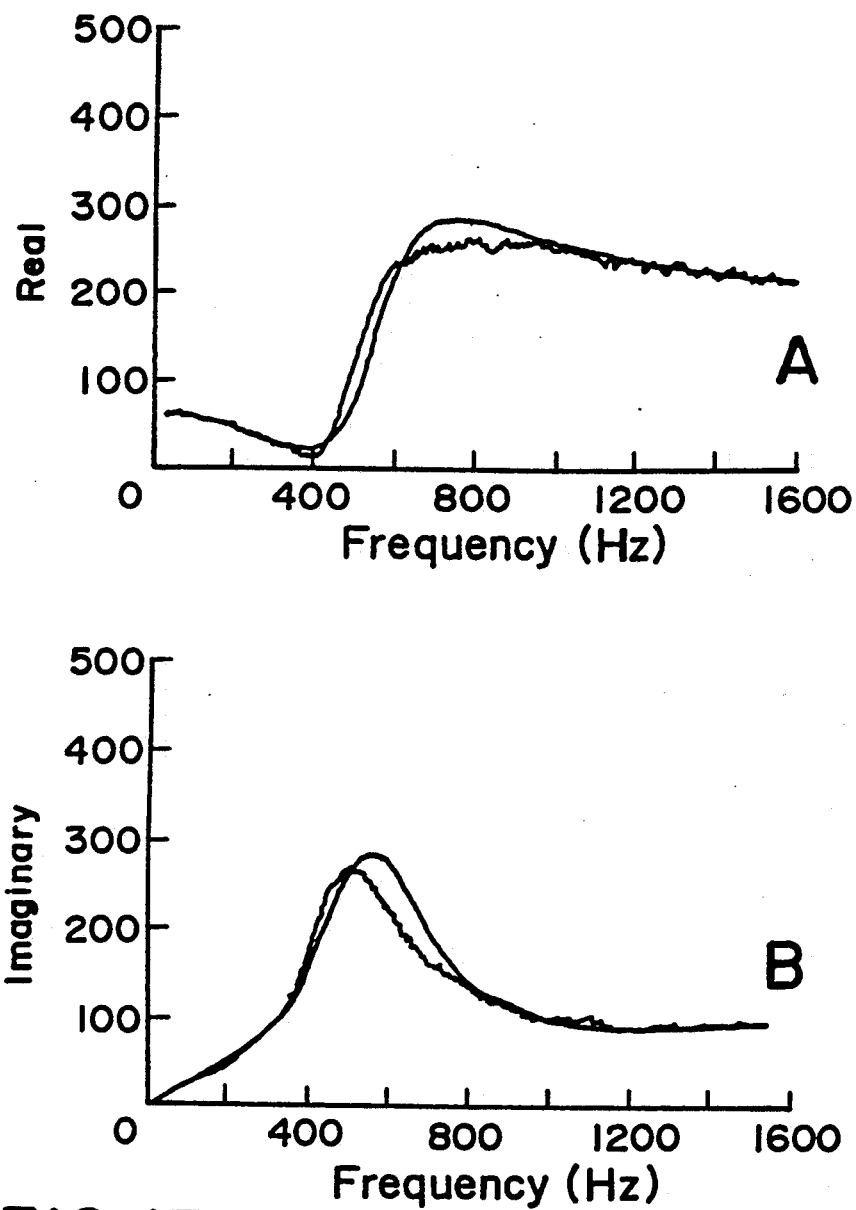
FIGS. 13A and 13B are show best-fit curve fitting to real (A) and imaginary (B) force/displacement curves, according to the BONE 5 algorithm.

FIGS. 13A and 13B show typical real (13A) and imaginary (13B) force/displacement curves (jagged lines) obtained from the ulna. The smooth lines in the figure represent the best curve fit by the BONE 5 program after several iterations and convergence of the $K_b$ values. The physical model used for determining physical parameters relating to skin and bone motion is the most accurate of the three algorithms described herein, in that a material damping term $E_s$ is included which is independent of frequency. In addition, there is a damping coefficient $\beta_s$ included which is dependent on frequency, to account for the propagation of energy away from the probe through the soft tissue parallel to the path between the probe and the bone.

The system above assumes that the reference structure indicated at 88 in FIG. 11 is fixed, i.e., that the arm or leg being monitored is rigidly held by the two end supports. In some test subjects, more precise bone parameter values are obtained using an algorithm which takes into account coupled movement between the fixed supports and the supported tissue regions. The algorithm is based on the behavior of the model mechanical system illustrated in FIG. 14. The system illustrated here includes, in addition to the components in the FIG. 11 system, a secondary reference structure 90 coupled to the primary reference structure 93 through a spring 92 having a spring constant $K_r$. In this model, the secondary structure represents the immobilized supports, the primary structure, the immobilized limb, and spring 92, the soft-tissue coupling between the limb and supports. The more complex system can be solved by the method of successive approximations by curve fitting, substantially as above, but additionally requiring a third curve-fitting operation with each iteration. Specifically, after calculating soft-tissue parameters from the high-frequency regions of the real and imaginary curves, and bone parameters from the subtracted low-frequency regions of the curves, spring constant $K_r$ is solved by curve fitting to the curves from which both skin and bone motion have been removed. Thereafter, each iteration involves a subtraction of two motions from high, low or total curve regions, for estimating new skin, bone or reference parameters. The algorithm is carried out until suitable convergence of bone stiffness values occurs, substantially in accordance with the BONE 5 program, as modified to include the additional curve subtraction and curve fitting required with each curve fitting.

Figure 14:
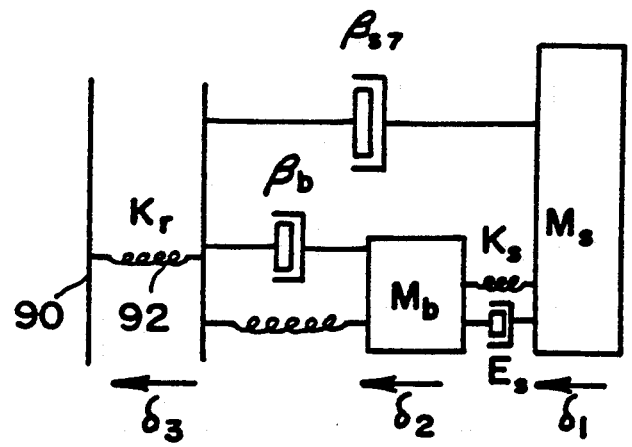
FIG. 14 illustrates a second-order linear mechanical system for modeling both soft-tissue damping and tissue-supporting spring effects.

It is seen that the BONE 5 algorithm, based on the system of FIG. 11 or 14, yields, in addition to bone stiffness values (determined from $K_b$), values for bone mass $M_b$ and a bone damping coefficient ($\beta_b$). The bone mass calculation provides information about bone density which heretofore has only been measurable only by X-ray or photon absorption techniques.

In addition, the algorithm described in this section yields values of various soft-tissue properties, including soft tissue mass ($K_s$), spring constant ($K_s$), damping ($B_s$) and material viscosity ($E_s$). To the extent one or more of these properties is correlated with physiological or disease states, such as localized tumor formation, or healing in injured soft tissue, these measurements are expected to be useful in diagnosing soft tissue conditions and/or monitoring healing or response to therapy.

D. Third Algorithm: POLE-ZERO

Figure 15:
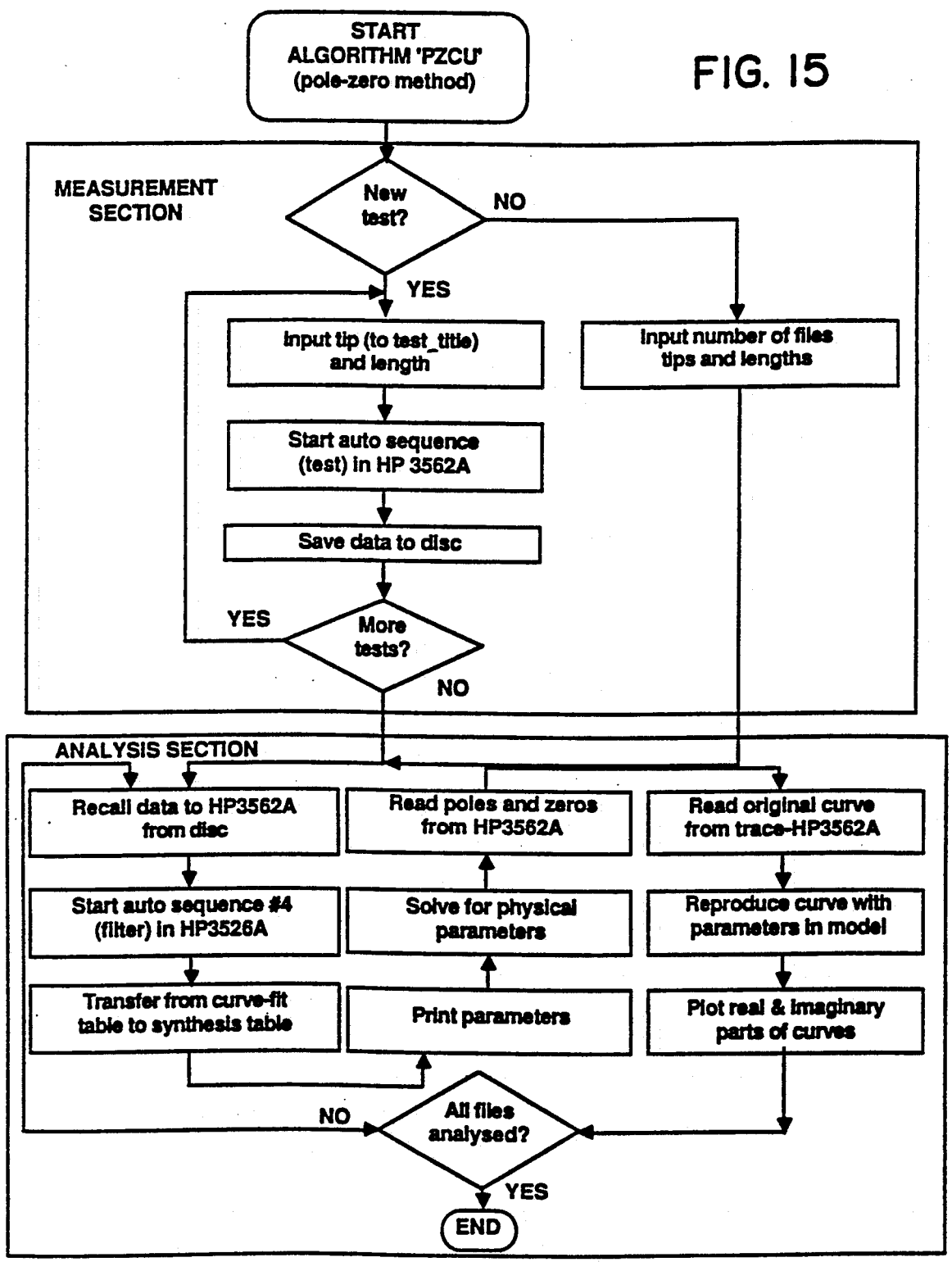
FIG. 15 is a flow chart of the POLE-ZERO algorithm, based on the behavior of the FIG. 11 mechanical system.
Figure 16:
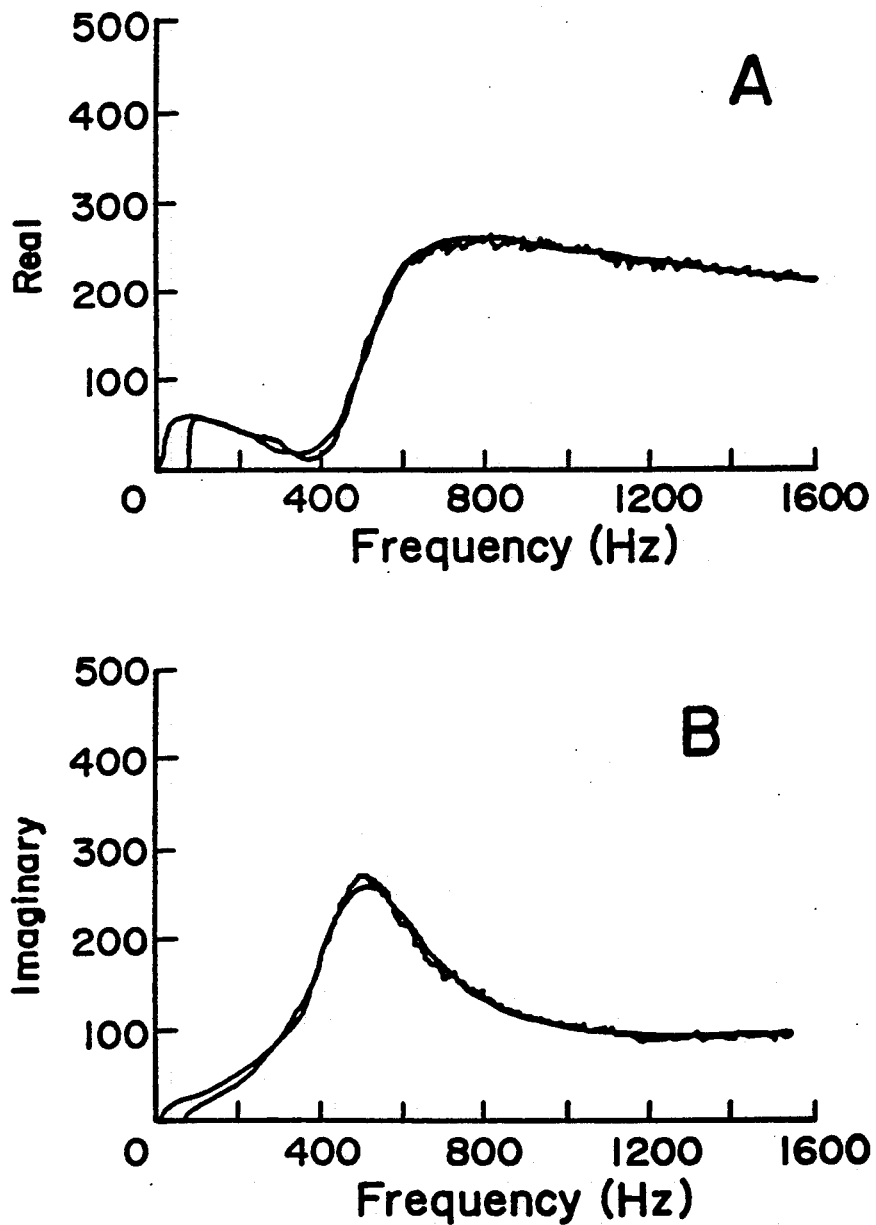
FIGS. 16A and 16B are show best-fit curve fitting to real (A) and imaginary (B) force/displacement curves, according to the POLE-ZERO algorithm.

This section describes a third algorithm for determining physical parameters relating to the equation of motion of a linear system with two degrees of freedom such as the system shown in FIG. 11. The algorithm employed is shown in FIG. 15. As seen in the figure, the algorithm includes a measurement section 120 for receiving data input and an analysis section 122 which performs the pole-zero calculations now to be described. The approach uses the curve fitting routine which is contained, for example,, in the HP3562A analyzer. This is a state-of-the art routine for finding the analytical representation of a general transfer function of the form:

$$\frac{F}{\delta} = G\frac{(s-z_1)(s-z_2)\ldots(s-z_n)}{(s-p_1)(s-p_2)\ldots(s-p_m)} \quad (16)$$

where G is a gain factor, $Z_1$ through $Z_n$ the zero values at which the numerator is zero, and $P_2$ through $P_n$ are the pole values at which the denominator is zero. The zero values represent the resonance frequencies of the transfer function, where tissue stiffness values are zero, and the pole values represent the anti-resonance values where bone stiffness values are large. The transfer function representing the mechanical system illustrated in FIG. 11 takes the form:

$$\frac{F}{\delta} = G\frac{(s-z_1)(s-z_2)(s-z_3)(s-z_4)}{(s-p_1)(s-p_2)} \quad (17)$$

where the four (s-$z_i$) terms represent two complex conjugate pairs, one for each degree of freedom in the system, and the two (s-$p_i$) terms, the poles for each degree of freedom. Here it is noted that the poles and zeros are assumed to be complex conjugate pairs, which excludes the possibility of modeling of the material damping factor of the skin ($E_s$) which is a frequency independent term. The analyzer determines the gain G and six pole-zero values in the transfer function by curve fitting to the real and imaginary force/displacement curves which represent the response of the tissue to excitation, as above. FIG. 16 shows the best fit (smooth lines) obtained by pole-zero analysis applied to the real and imaginary force/displacement curves (jagged lines) for bone response measurements in an ulna. As seen, the pole-zero approach has the advantage of a better curve fit than the BONE 5 algorithm above. However, as indicated above, the present approach has the disadvantage that the skin material damping term cannot be modeled.

The physical parameters corresponding to the pole-zero values are determined by adding the skin mass and bone mass terms in the equation of motion of the FIG. 11 system (without the material damping term), and converting the equation to a ratio of two polynomials in the form of equation 17. The seven physical parameters of the system (mass, spring constant, and damping coefficient for both bone and skin; and a frequency-independent material damping factor) are now determined from the gain and six pole-zero values. As above, bone stiffness and a weight-bearing parameter can be calculated from the determined $K_b$ value. The POLE-ZERO program designed to perform the correlation of gain and pole-zero factors with the physical parameters of the mechanical system is detailed in Appendix B. The program is written in BASIC program language and can be run on a Hewlett-Packard Model HP9826 computer.

E. Comparison of the Three Algorithms

The relative performance of the three algorithms described above was examined, using each algorithm to determine $K_s$ and $K_b$ values for each of five measurements made on the right and left ulna of a human subject. The results are shown in Table I below. "Diff" denotes the difference between the maximum and minimum of the five tests. Note that the skin stiffness tends to be low for the first test, then increases with subsequent tests, as would be expected with continued probe pressure against the arm.

| Test | STO-ANALY K(skin) | K (bone) | K(skin) | BONES K(bone) | K(skin) | POLE K(bone) |
|---|---|---|---|---|---|---|
| RU21 | 192 | 116 | 182 | 128 | 191 | 134 |
| RU22 | 196 | 127 | 180 | 131 | 185 | 129 |
| RU23 | 225 | 122 | 220 | 128 | 227 | 142 |
| RU24 | 207 | 128 | 199 | 131 | 207 | 136 |
| RU25 | 247 | 129 | 239 | 140 | 250 | 149 |
| Avg= | | 124 | | 132 | | 138 |
| Diff= | 55 | 13 | 59 | 12 | 65 | 20 |
| Diff/Avg= | | 0.10 | | 0.09 | | 0.15 |
| LU21 | 148 | 149 | 159 | 134 | 165 | 144 |
| LU22 | 192 | 137 | 193 | 127 | 202 | 151 |
| LU23 | 194 | 133 | 193 | 133 | 202 | 150 |
| LU24 | 199 | 137 | 197 | 134 | 206 | 153 |
| LU25 | 188 | 147 | 195 | 133 | 200 | 153 |
| Avg= | | 141 | | 132 | | 150 |
| Diff= | 51 | 14 | 38 | 7 | 41 | 9 |
| Diff/Avg= | | 0.10 | | 0.05 | | 0.06 |

The STO-ANALY algorithm is the fastest and simplest, but is also the least accurate, since it does not consider skin mass and damping effects. The BONE 5 algorithm, which is modeled as a two-degree of freedom spring-mass system with realistic material damping, gives the most consistent measure of bone stiffness. The POLE-ZERO algorithm, which employs accurate curve fitting, but does not include frequency dependent soft-tissue damping, gives more consistent bone stiffness values than STO-ANALY, but is less consistent than BONE 5.

IV. Utility

One important use of the present invention is in the diagnosis of osteoporosis, and monitoring of treatment modalities. Earlier studies conducted by the inventor and co-workers indicates a good correlation between bone stiffness, as measured by mechanical response in vibrated tissue, and bone mineral content in experimental-tissue osteoporosis in monkeys (Young, 1982). Thus, bone stiffness values determined in accordance with the present invention would provide accurate diagnosis of osteoporosis conditions. Assuming the test subject does not have abnormally heavy fat of muscle tissue, the STO-ANALY algorithm can provide a rapid measure of bone stiffness. For more accurate and reproducible values, the BONE 5 or POLE-ZERO approaches would be preferred. The latter algorithms—which additionally provide bone mass data—would allow for a more detailed analysis of bone condition.

The primary bone parameters which are determined in the invention—bone stiffness and weight loading—are both important indicators of fracture healing, making the method useful as a means for monitoring bone healing. No other method for making an accurate assessment of bone stiffness is available, and the present method can be applied even when excessive tissue bulk is present. Where bone mass is also calculated (using the BONE 5 or POLE-ZERO approach), the method can be used to provide information about bone matrix condition, as a tool for diagnosing or monitoring the treatment of bone disorders where the bone matrix is an important feature of the disease.

It may be advantageous, particularly in monitoring fracture healing, to construct a profile of bone stiffness or other bone or soft-tissue parameter along the length of the bone being examined. This can be done, according to the invention, by making the relevant physical parameter measurements at selected points along the length of the bone, and constructing a profile of the parameter(s) along the length of the bone.

The invention may also be used to provide physical measurements on soft tissue only, again using either the BONE 5 or POLE-ZERO approach.

The method is rapid, virtually painless, and unlike conventional photon absorptivity measurements, does not involve exposure to radiation. Only brief training is needed for operating the apparatus, and the apparatus itself is considerably less expensive and faster than conventional photon absorptivity devices.

While the invention has been described in detail with respect to specific apparatus, algorithms, and uses, it will be appreciated that various changes and modifications can be made without departing from the invention.

It is claimed:

1. A computer-assisted method for determining bone cross-sectional bending stiffness in a subject, comprising
    placing a vibratory unit against the region of the bone whose bending stiffness is to be determined,
    exciting the vibratory unit, with such pressed against said bone region, in a frequency range substantially in the frequency range of 70–1,600 Hertz,
    measuring the frequency-dependent mechanical response said bone region within such frequency range, and converting the response measurements to real and imaginary frequency-dependent force/displacement curves,
    solving the equations of motion of a linear mechanical system (a) having a soft-tissue mass Ms, a soft-tissue spring constant Ks, soft-tissue damping factor $\beta$s, a bone mass Mb, a bone spring constant Kb, and a bone damping factor $\beta$b, and (b) characterized by a equation of motion having real and imaginary curves, and
    by said solving, determining a value of $K_b$ which corresponds to the bone bending stiffness in the excited bone region.

2. The method of claim 1 wherein the vibratory unit is excited by a white noise frequency generator.

3. The method of claim 1, wherein said solving step includes (a) estimating $K_s$, $M_s$, and $\beta_s$, by curve fitting to high-frequency regions of the real and imaginary force/displacement curves, substantially above 800 Hertz, (b) subtracting the estimated $K_s$, $M_s$ and $\beta_s$ values from low-frequency regions of these curves substantially below 800 Hertz, yielding corrected low-frequency curves, (c) estimating $K_b$, $M_b$, and $\beta b$ by curve fitting to the corrected low-frequency curves, (d) subtracting the estimated $K_b$, $M_b$, and $\beta_b$ values from the high-frequency regions of the curves, yielding corrected high-frequency curves, (e) estimating new $K_s$, $M_s$, and $\beta s$ values by curve fitting to the corrected high frequency curves, and (f) repeating steps (b)-(e) until changes in the estimated $K_b$ value converge to a selected limit.

4. The method of claim 3, wherein the linear mechanical system representing the bone region includes a frequency-independent material damping coefficient $E_s$ and said curve fitting to the high-frequency regions of the curve is further used to calculate $E_s$.

5. The method of claim 1, wherein said solving step includes the steps of representing the equation of motion of the mechanical system as a transfer function of the form:

$$F/\delta = G \, (S-Z_1)(S-Z_2)(S-Z_3)(S-Z_4) / (S-P_1)(S-P_2)$$

where G is the gain factor, $Z_1-Z_4$ are the zero values at which the numerator of the transfer function is zero, and $P_1$ and $P_2$ are the pole values at which the denominator is zero, determining the gain and the zero and pole values by curve fitting to the real and imaginary force/displacement curves, and calculating the $M_s$, $K_s$, $\beta_s$, $M_b$, $K_b$, $\beta_b$, values from the determined gain and zero and pole values.

6. The method of claim 1, for use in determining a stiffness profile along a long bone, wherein bone stiffness is determined from $K_b$ measurements made at spaced points along the length of the bone, and the bone stiffness data obtained is used to construct a stiffness profile along the length of the bone.

7. Apparatus for determining bone cross-sectional bending stiffness in a subject, comprising
a vibratory unit adapted to be placed against the region of the bone whose bending stiffness is to be determined,
a frequency generator for exciting the vibratory unit, with such pressed against the bone region, in a frequency range substantially in the range 70-1,600 Hertz,
an analyzer designed to measure the frequency-dependent mechanical response of the tissue within such frequency range, and convert the response measurements to real and imaginary frequency-dependent force/displacement curves,
computational means for solving the equations of motion of a mechanical system having a soft-tissue mass Ms, a soft-tissue spring constant Ks, soft-tissue damping factor $\beta$s, a bone mass Mb, a bone spring constant Kb, and a bone damping factor $\beta$b of said mechanical system, by fitting the real and imaginary equation-of-motion behavior of the mechanical system to the real and imaginary force/displacement curves, thereby to determine the value of Kb which corresponds to the bone bending stiffness in the excited bone region.

8. The apparatus of claim 7, wherein the vibratory unit includes an electromagnetic shaker having a vibratory piston, an impedance head with force and acceleration transducers carried on the exciter, and attached to the impedance head, a probe which defines a concave tissue-contact surface.

9. The apparatus of claim 8, wherein the probe is mechanically coupled to the impedance head through a ball-and-socket coupling.

10. The apparatus of claim 7, wherein said computational means is operative to (a) estimate $K_s$, $M_s$, and $\beta_s$, by curve fitting to high-frequency regions of the real and imaginary force/displacement curves, substantially above 800 Hertz, (b) subtract the estimated $K_s$, $M_s$ and $\beta_s$ values from low-frequency regions of these curves substantially below 800 Hertz, yielding corrected low-frequency curves, (c) estimate $K_b$, $M_b$, and $\beta_b$ by curve fitting to the corrected low-frequency curves, (d) subtract the estimated $K_b$ $M_b$, and $\beta_b$ from the high-frequency regions of the curves, yielding corrected high-frequency curves, (e) estimate new $K_s$, $M_s$ and $\beta_s$ values by curve fitting to the corrected high frequency curves, and (f) repeat steps (b)-(e) until changes in the estimated $K_b$ value converge to a selected limit.

11. The apparatus of claim 7, wherein said the equation of motion of the mechanical system is represented as a transfer function of the form:

$$F/\delta = (S-Z_1)(S-Z_2)(S-Z_3)(S-Z_4) / (S-P_1)(S-P_2)$$

where G is the gain factor, $Z_1-Z_4$ are the zero values at which the numerator of the transfer function is zero, and $P_1$ and $P_2$ are the pole values at which the denominator is zero, and said computational means is designed to determine the gain and the zero and pole values by curve fitting to the real and imaginary force/displacement curves, and to calculate the $M_s$, $K_s$, $\beta_s$, $M_b$, $K_b$, $\beta_b$, values from the determined gain and zero and pole values.

* * * * *